US007482159B2

(12) United States Patent
Cano García et al.

(10) Patent No.: US 7,482,159 B2
(45) Date of Patent: Jan. 27, 2009

(54) SNAIL, A NEW MARKER FOR TUMOUR INVASION AND TARGET PROTEIN OF NEW ANTITUMORAL COMPOUNDS

(75) Inventors: Amparo Cano García, Madrid (ES); M. Angela Nieto Toledano, Madrid (ES); M. Isabel Rodrigo Castro, Madrid (ES); Annamaria Locascio, Madrid (ES); Marta García del Barrio, Madrid (ES); María José Blanco Fernandez de Valderrama, Madrid (ES); Francisco Portillo Pérez, Madrid (ES); Mirna Alicia Pérez Moreno, Madrid (ES)

(73) Assignees: Consejo Superior de Investigaciones Cientificas, Madrid (ES); Universidad Autonoma de Madrid Ciudad Universitaria de Cantoblanco Crta, Madrid (ES)

( * ) Notice: Subject to any disclaimer, the term of this patent is extended or adjusted under 35 U.S.C. 154(b) by 0 days.

(21) Appl. No.: 11/599,664

(22) Filed: Nov. 15, 2006

(65) Prior Publication Data
US 2007/0065450 A1     Mar. 22, 2007

Related U.S. Application Data

(62) Division of application No. 10/461,256, filed on Jun. 13, 2003, which is a division of application No. 09/806,445, filed as application No. PCT/ES00/00226 on Jun. 27, 2000, now Pat. No. 6,617,121.

(30) Foreign Application Priority Data
Jul. 1, 1999     (ES) ................................... 9901466

(51) Int. Cl.
C12N 15/85     (2006.01)
(52) U.S. Cl. ....................................................... 435/455
(58) Field of Classification Search ........................ None
See application file for complete search history.

(56) References Cited

FOREIGN PATENT DOCUMENTS

WO   WO 96/02002   1/1996
WO   WO 99/20168   4/1999

OTHER PUBLICATIONS

Gura (Science, 1997, 278:1041-1042).*
Jain (Sci. Am., 1994, 271:58-65).*
Yuen et al., (Jun. 1, 2000, Froniters in Bioscience, vol. 5, d588-593, title; Clinical Studies of Antisense Therapy in Cancer).*
Sczakiel, G, (Froniters in Bioscience 5, d194-201, Jan. 1, 200I).*
Nakayama et al., Developmental Biology, 1998 Jul. 1;199(1):150-63.*
Twigg et al., 1999, Hum Genet, vol. 105, pp. 320-326.*
Curti (Crit. Rev. in Oncology/Hematology, 1993, 14:29-39).*
Hartwell et al (Science, 1997, 278:1064-1068).*
A. Cano et al., "The transcription factor Snail controls epithelial-mesenchymal transitions by repressing E-cadherin expression", Nature Cell Biology, 2(2): 76-83 (2002).
E. Batlle, "The transcription factor Snail is a repressor of E-cadherin gene expression in epithelial tumor cells", Nature Cell Biology, 2: 84-89 (2000)in.
H. Nakayama et al., "The transition to endoreduplication in Trophoblast Giant Cells is Regulated by the mSNA Zinc Finger . . . ", Developmental Biology, 199: 150-163 (1998).
O. Hiroki et al., "Dynamic Behavior of the Cadherin-Based Cell-Cell Adhesion System during Drosophila Gastrulation", Development Biology, 203: 435-450 (1998).
S. Pierre et al., "The Zinc-Finger Protein Slug Causes Desmosome Dissociation . . . ", The Journal of Cell Biology, 137:1403-1419 (1997).
N. Fuse et al., "Diploidy of Drosophila imaginal cells is maintained by transcriptional repressor encoded by escargot", Genes and Development, 8: 2270-2281 (1994).
D. Smith, "Isolation of Sna, a mouse gene homologous to the Drosophila genes snail and escargot: its expression pattern . . . ", Development, 116: 1033-1039 (1992).
M.J.G. Bussemakers et al., "Transcriptional regulation of the human E-cadherin gene in human . . . " Biochemical and Biophysical Research Communication, 203(2): 1284-1290 (1994).
L. Fu et al., "Translation regulation of human p53 gene expression", EMBO J, 15(16): 4392-4401 (1996) [Abstract only].
R.P. Hill, "The Basic Science of Oncology", Tannock et al., Eds, McGraw Hill, NY, pp. 178-195 (1992).
T.L. Frazndsen et al., "Assays for the Study of Human Cancer Invasion and Metastasis", Fibrinolysis, 6(4): 71-76 (1992).
M. Blanco et al., "Correlation of Snail expression with histological grade and lymph node status in breast carcinomas", Oncology, 21: 3241-3246 (2002).
W.A. Paznekas et al., "Genomic organization, expression, and chromosome location of the human Snail gene (SNAI1) and a related processed . . . ", Genomics, 62: 42-49 (1999).
S.R. Twigg et al., "Characterization of the human snail (SNAI1) gene and exclusion as a major disease gene in craniosynostosis", 105: 320-326 (1999).
A. Mialhe et al., "Expression of E-Cadherin and alpha, beta and gamma-Catenins in Human Bladder Carcinomas . . . ", Invasive Metastasis, 17: 124-137 (1997).
K. Schofield et al., "The Cell Adhesion Molecule, E-Cadherin, Distinguishes Mesothelial Cells from Carcinoma Cells in Fluids", Cancer, 81(5): 293-298 (1997).
B. Alberts et al., "Differentiated Cells and the . . . ", Molecular Biology of the Cell, 2nd ed., Garland Publishing Inc., NY and London, Ch 17, pp. 951-952 & Ch 21, pp. 1188-1190.
T. Saito et al., "E-Cadherin Gene Mutations Frequently Occur in Synovial Sarcoma as a Determinant of Histological Features", American Journal of Pathology, 159(6): 2117-2124.

(Continued)

Primary Examiner—Misook Yu
(74) Attorney, Agent, or Firm—Dann, Dorfman, Herrell and Skillman, P.C.; Patrick J. Hagan, Esq.

(57) ABSTRACT

The Snail transcription factor has been identified as a repressor of the expression of E-cadherin. The expression of Snail induces invasive and metastatic capacity in tumor cells. This invention presents: a new target protein, Snail, for the identification of new antitumoral compounds and a new diagnostic tumor marker, indicative of tissue invasion and metastatic capacity.

4 Claims, 6 Drawing Sheets

OTHER PUBLICATIONS

R. Silye et al., "E-Cadherin/Catenin complex in Benign and Malignant Melanocytic Lesions", Journal of Pathology, 186: 350-355 (1998).

D. S. Sanders et al., "Alterations in cadherin and catenin expression during the biological progression of melanocytic tumours", Mol. Pathol., 52(3): 151-157 (1999) [Abstract only].

I. Poser et al., "Loss of E-cadherin Expression in Melanoma Cells Involves Up-regulation of the . . . ", The Journal of Biological Chemistry: 276(27): 24661-24666 (2001).

A. Tang et al., "E-cadherin is the major mediator of human melanocyte adhesion to keratinocytes in vitro", Journal of Cell Science, 107: 983-992 (1994).

E. H. J. Danen et al., "E-cadherin expression in human melanoma", Melanoma Research, 6: 127-131 (1996).

Yuen et al., "Clinical Studies of Antisense Therapy in Cancer", Frontiers in Bioscience, vol. 5, d588-593 (2000).

G. Sczakiel, Frontiers in Bioscience, 5: 194-201 (2001).

A. Barrallo-Gimeno et al., "The Snail genes as inducers of cell movement and survival: implications in development and cancer", Development, 132: 3151-3161 (2005).

W. Birchmeier et al., "Cadherin expression in carcinomas: role in the formation of cell junctions and the prevention of invasiveness", Biochemica et Biophysica Acta, 1198: 11-26 (1994).

C. Burdsal et al., "The role of E-cadherin and integrins in mesoderm differentiation and migration at the mammalian primitive streak", Development, 118: 829-844 (1993).

J. Cross et al., "Hxt encodes a basic helix-loop-helix transcription factor that regulates trophoblast cell development", Development, 121(8): 2513-23 (1995).

B. Craene et al., "Unraveling signalling cascades for the Snail family of transcription factors", Cellular Signalling, 17: 535-547 (2005).

C. Espineda et al., "Repression of Na, K-ATPase, B1-Subunit by the Transcription Factor Snail in Carcinoma", Molecular Biology of the Cell, 15: 1364-1373 (2004).

T. Faria et al., "Trophoblast Cell Differentiation: Establishment, Characterization, and Modulation of a Rat Trophoblast Cell Line Expressing Members of the Placental Prolactin Family", Endocrinology, 129(6): 2895-2906 (2004).

N.K. Kurrey et al., "Snail and Slug are major determinants of ovarian cancer invasiveness at the transcription level", Gynecologic Oncology, 97: 155-165 (2005).

P. Navarro et al., "A Role for the E-Cadherin Cell-Cell Adhesion Molecule during Tumor Progression of Mouse Epidermal Carcinogenesis", The Journal of Cell Biology, 115(2): 517-533 (1991).

M. Nieto et al., "Cloning and developmental expression of Sna, a murine homologue of the Drosophila snail gene", Development, 116: 227-237 (1992).

M. Nieto, "The Snail Superfamily of Zinc-Finger Transcription Factors", Nature Reviews, Molecular Cell Biology, 3: 155-166 (2002).

T. Okubo et al., Down-Regulation of Promoter I.3 Activity of the Human Aromatase Gene in Breast Tissue by Zinc-finger Protein, Snail (SnaH), Cancer Research, 61: 1338-1346 (2001).

D. Olmeda et al., "SNAI1 is Required for Tumor Growth and Lymph Node Metastasis of Human Breast Carcinoma MDA-MB-231 Cells", Cancer Res., 67(24): 11721-11731 (2007).

D. Olmeda et al., "Snai1 and Snai2 collaboarte on tumor growth and metastasis properties of mouse skin carcinoma cell lines", Oncogene, 1-12 (2008).

H. Peinado et al., "Snail Mediates E-Cadherin Repression by the Recruitment of the Sin3A/Histone Deacetylase 1 (HDAC1)/HDAC2 Complex", Molecular and Cellular Biology, 24(1): 306-319 (2004).

H. Peinado et al., "Snail, ZEB and bHLH factors in tumour progression: an alliance against the epithelial phenotype?", Nature Reviews, Cancer, 7: 415-428 (2007).

J. Schipper et al., "E-Cadherin Expression in Squamous Cell Carcinomas of Head and Neck: Inverse Correlation with Tumor Dedifferentiation and Lymph Node Metastasis", Cancer Research, 51: 6328-6337 (1991).

M. Sefton et al., "Conserved and divergent roles for members of the Snail family of transcription factors in the check and mouse embryo", Development, 125: 3111-3121 (1998).

M. Takeichi, "The cadherins: cell-cell adhesion molecules controlling animal morphogenesis", Development, 102: 639-655 (1988).

M. Takeichi, "Cadherins in cancer: implications for invasion and metastasis", Cell Biology, 5: 806-811 (1993).

M. Takeichi, "Morphogenetic roles of classic cadherins", Cell Biology, 7: 619-627 (1995).

J. Thiery, "Epithelial-Mesenchymal Transitions in Tumour Progression", Nat. Rev. Cancer, 2: 442-454 (2002).

J. Theiry et al., "Complex networks orchestrate epithelial-mesenchymal transitions", Nature Reviews, Molecular Cell Biology, 7: 131-142 (2006).

* cited by examiner

Fig. 1A
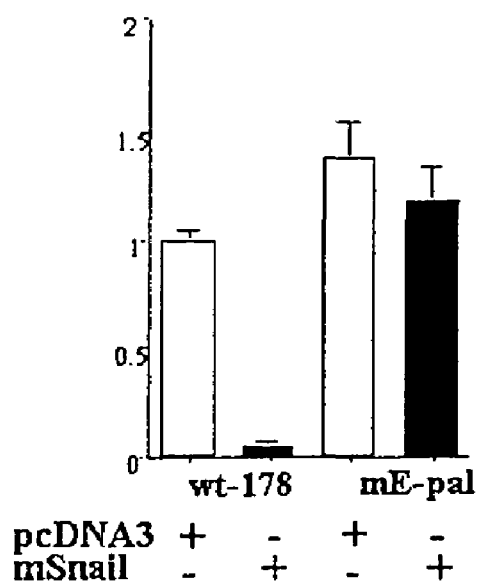
Fig. 1B
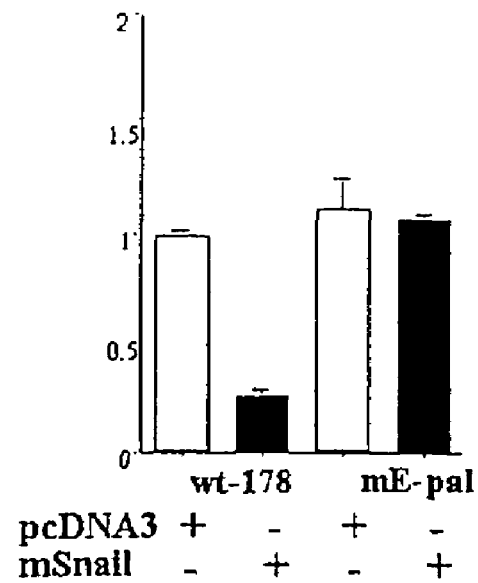
Figure 1

SNAIL, A NEW MARKER FOR TUMOUR INVASION AND TARGET PROTEIN OF NEW ANTITUMORAL COMPOUNDS

CROSS-REFERENCE TO RELATED APPLICATIONS

This application is a divisional of U.S. application Ser. No. 10/461,256, filed Jun. 13, 2003, which is a divisional of U.S. application Ser. No. 09/806,445, filed Oct. 18, 2001 now U.S. Pat. No. 6,617,121, as the U.S. National Stage of International Application No. PCT/ES00/00226, filed Jun. 27, 2000. The disclosures of the aforesaid applications are incorporated by reference in their entireties in the present application.

PRIOR ART

The protein E-cadherin has not only been shown to mediate intercellular adhesion of epithelial cells during embryonic development and in adult tissues, but also to be implicated in the phenotypic transformation observed in epithelial tumours during their progression into invasive tumours. In this process, of invasion by the tumour cells, expression of the protein E-cadherin is reduced or abolished and this loss is associated with the acquisition of migratory properties. Functional alterations of E-cadherin and/or its associated proteins, catenins, have been associated with de-differentiation and greater aggressivity of tumours [Takeichi, M. Cadherins in cancer: implications for invasion and metastasis. Curr. Op. Cell Biol. 5, 806-811 (1993); Birchmeier, W. & Behrens, J. Cadherin expression in carcinomas: role in the formation of cell junctions and the prevention of invasiveness. Biochim. Biophys. Acta 1198, 11-26 (1994)] and have even been seen to be implicated in the transition from adenomas to invasive carcinomas [Perl, A. K., P. Wilgenbus, U. Dahl, H. Semb & Christofori, G. A causal role for E-cadherin in the transition from adenoma to carcinoma. Nature 392, 190-193 (1998).]. For all of these reasons, the E-cadherin gene has been considered to be a tumoral invasion suppressor gene [Frixen, U. H., et al. E-cadherin-mediated cell-cell adhesion prevents invasiveness of human carcinoma cells. J. Cell Biol 113, 173-185 (1991); Vleminckx, K., Vakaet, L. J., Mareel, M., Fiers, W. & Van Roy, F. Genetic manipulation of E-cadherin expression by epithelial tumor cells reveals an invasion suppressor role. Cell 66, 107-119 (1991); Miyaki, M. et al. Increased cell-substratum adhesion, and decreased gelatinase secretion and cell growth, induced by E-cadherin transfection of human colon carcinoma cells. Oncogene 11, 2547-2552 (1995); Llorens, A. et al. Down regulation of E-cadherin in mouse skin carcinoma cells enhances a migratory and invasive phenotype linked to matrix metalloproteinase-9 gelatinase expression. Lab. Invest. 78, 1-12 (1998).] so that the molecular mechanisms which control its expression or function are of the utmost importance in increasing our knowledge of tumour invasion processes.

Expression of the E-cadherin gene is regulated by several elements located in the 5' proximal region of its promoter [Behrens, J., Löwrick, O., Klein, H. L. & Birchmeier, W. The E-cadherin promoter: functional analysis of a GC-rich region and an epithelial cell-specific palindromic regulatory element. Proc. Natl. Acad. Sci. USA 88, 11495-11499 (1991); Ringwald, M., Baribault, H., Schmidt, C. & Kemler, R. The structure of the gene coding for the mouse cell adhesion molecule uvomorulin. Nucleic Acids Res. 19, 6533-6539 (1991); Bussemakers, M. J., Giroldi, L. A., van Bokhoven A. & Schalken, J. A. Transcriptional regulation of the human E-cadherin gene in human prostate cancer cell lines: characterization of the human E-cadherin gene promoter. Biochem. Biophys. Res. Commun. 203, 1284-1290 (1994); Giroldi, L. A. et al. Role of E-boxes in the repression of E-cadherin expression. Biochem. Biophys. Res. Commun. 241, 453-458 (1997)]. Of these, the E-pal element, which contains two E-boxes, has been identified in the E-cadherin promoter in mice (between positions −90 and −70) and is important because it acts as a repressor in normal cells and transformed cells deficient in E-cadherin [Behrens, J., Löwrick, O., Klein, H. L. & Birchmeier, W. The E-cadherin promoter: functional analysis of a GC-rich region and an epithelial cell-specific palindromic regulatory element. Proc. Natl. Acad. Sci. USA 88, 11495-11499 (1991); Hennig, G., Löwrick, O., Birchmeier, W & Behrens, J. Mechanisms identified in the transcriptional control of epithelial gene expression. J. Biol. Chem. 271, 595-602 (1996); Faraldo; M. L., Rodrigo, I., Behrens, J., Birchmeier, W & Cano, A. Analysis of the E-cadherin and P-cadherin promoters in murine keratinocyte cell lines from different stages of mouse skin carcinogenesis. Mol. Carcinog. 20, 33-47 (1997); Rodrigo, I., Cato, A. C. B. & Cano, A. Regulation of E-cadherin gene expression during tumor progression: the role of a new Ets-binding site and the E-pal element. Exp. Cell Res. 248, 358-371 (1999)]. The transcription factors which interact with this element or in the corresponding region of the promoter of the human cadherin gene [Bussemakers, M. J., Giroldi, L. A., van Bokhoven A. & Schalken, J. A. Transcriptional regulation of the human E-cadherin gene in human prostate cancer cell lines: characterization of the human E-cadherin gene promoter. Biochem. Biophys. Res. Commun. 203, 1284-1290 (1994); Giroldi, L. A. et al. Role of E-boxes in the repression of E-cadherin expression. Biochem. Biophys. Res. Commun. 241, 453-458 (1997)] are unknown.

Potential transcription factors which are repressors of the expression of the E-cadherin gene could be of great value in the identification of new antitumoral candidates which act by inhibiting the function of these factors, and consequently the invasive and metastatic process. Furthermore, their presence could be used as markers of tumour spread and malignancy.

DESCRIPTION

Brief Description

The transcription factor Snail has been identified as a repressor of the expression of E-cadherin, as it has a direct interaction with the E2 box of the E-pal element of the promoter. The ectopic expression of Snail in epithelial cells induces epithelial-mesenchymal transition and the acquisition of migratory properties concomitant with inhibition of E-cadherin expression and the loss of other epithelial differentiation markers. This invention presents and includes the following:

a new target protein for the identification of new antitumoral compounds, and a new marker of tumour invasion and metastasis and its application as a diagnostic marker of the disease and as a guide to medical professionals in the selection or evaluation of treatments.

Detailed Description

Snail is a Transcription Factor which Acts as a Direct Repressor of E-cadherin Expression.

Identification of transcription factors which interact with the E-pal element was undertaken by means of a one-hybrid approximation using the mouse E-pal sequence (−90/−70) oligomerised to direct the expression of the HIS3 gene of *S. cerevisiae* as bait and a cDNA gene library of NIH3T3 fused to the GAL4 activation domain as a prey. A total of 130 clones were isolated, capable of interacting with (and directing the transcription of the reporter gene HIS3) the construction containing the native E-pal element; they did not recognise the mutated oligomeric element. This mutated form of the E-pal element contains 2 modified bases (TT instead of GC) which eliminate the E2 box. This mutated form has been described as being responsible for abolishing the repressor effect in the E. cadherin promoter in mice [Hennig, G., Löwrick, O., Birchmeier, W. & Behrens, J. Mechanisms identified in the transcriptional control of epithelial gene expression. J. Biol. Chem. 271, 595-602 (1996); Faraldo, M. L., Rodrigo, I., Behrens, J., Birchmeier, W & Cano, A. Analysis of the E-cadherin and P-cadherin promoters in murine keratinocyte cell lines from different stages of mouse skin carcinogenesis. Mol. Carcinog. 20, 33-47 (1997).

Sequentiation of the isolated clones revealed that 49% of them contained inserts which encoded the complete or partial sequence of the mouse Snail cDNA [Nieto, M. A., Bennet, M. F., Sargent, M. G. & Wilkinson, D. G. Cloning and developmental expression of Sna, a murine homologue of the *Drosophila* snail gene. *Development* 116, 227-237 (1992); Smith, D. E., Del Amo, F. F. & Gridley, T. Isolation of Sna, a mouse homologous to the *Drosophila* gene snail and escargot: its expression pattern suggests multiple roles during postimplantation development. *Development* 116, 1033-1039 (1992)], while one single clone encoded a partial sequence of the mouse Slug cDNA.

To determine the effect of Snail as a transcription factor in the context of the proximal region of the E-cadherin promoter (−178/+92), the complete sequence of Snail DNA was subcloned in an expression vector (pcDNA3) and its activity was analysed by cotransfection in two mouse epidermal keratinocyte cell lines, MCA3D and PDV. Both lines had previously been characterised as having a high level of E-cadherin expression and promoter activity [Faraldo, M. L., Rodrigo, I., Behrens, J., Birchmeier, W & Cano, A. Analysis of the E-cadherin and P-cadherin promoters in murine keratinocyte cell lines from different stages of mouse skin carcinogenesis. Mol. Carcinog. 20, 33-47 (1997); Rodrigo, I., Cato, A. C. B. & Cano, A. Regulation of E-cadherin gene expression during tumor progression: the role of a new Ets-binding site and the E-pal element. Exp. Cell Res. 248, 358-371 (1999); Navarro, P. et al. A role for the E-cadherin cell-cell adhesion molecule in tumor progression of mouse epidermal carcinogenesis. J. Cell Biol. 115, 517-533 (1991)]. Cotransfection of Snail in MCA3D cells (FIG. 1A) and PDV (FIG. 1B) produced strong repression of the native E-cadherin promoter (95% and 75%, respectively), but not of the promoter containing the mutated E2 box (FIG. 1). These results confirm those obtained by the one-hybrid screening method and demonstrate that Snail is a direct repressor of the transcription of the E-cadherin gene acting through its binding to the E2 box of the E-pal element.

Snail Induces the Fibroblastic Conversion of Epithelial Cells and the Acquisition of Migratory Properties.

To obtain more information about the role of the Snail protein in the regulation of the E-cadherin gene and its participation in epithelial-mesenchymal transition, it was ectopically expressed in several cell lines. Transient expression of Snail was initially analysed in the keratinocyte lines MCA3D and PDV, which offer the advantage of being able to grow in isolated groups, establishing strong intercellular contacts mediated by E-cadherin even at low density, and exhibit very low cell motility [Navarro, P. et al. A role for the E-cadherin cell-cell adhesion molecule in tumor progression of mouse epidermal carcinogenesis. J. Cell Biol. 115, 517-533 (1991); Lozano, E & Cano, A. Cadherin/catenin complexes in murine epidermal keratinocytes: E-cadherin complexes containing either b-catenin or plakoglobin contribute to stable cell-cell contacts. Cell Adh. Commun. 6, 51-67 (1998); Gómez M., Navarro P. & Cano A. Cell adhesion and tumor progression in mouse skin carcinogenesis: increased synthesis and organization of fibronectin is associated with the undifferentiated spindle phenotype. Invasion & Metastasis 14, 17-26 (1994); Frontelo, P. et al. Transforming growth factor bi induces squamous carcinoma cell variants with increased metastatic abilities and a disorganized cystoskeleton. Exp. Cell Res. 244, 420-432 (1998)]. The overexpression of Snail eliminated intercellular contacts within the 24-28 hours after transfection in both cell types as a consequence of inhibition of the expression of E-cadherin (FIGS. 2b and 2f) and other associated proteins, such as plakoglobin. Simultaneously width these changes, the morphology of the cells transfected with Snail was greatly altered. Abundant membranous prolongations and long filaments resembling filopodia were observed in both cell lines.

Stable expression of Snail was carried out in the cell line MDCK, which exhibits a "prototypical" epithelial phenotype and appears as a monolayer in culture. This phenotype does not seem to be affected by expression of the control vector in six independent isolated clones (FIG. 3a), which maintain the expression of E-cadherin (FIG. 3b) and plakoglobin (FIG. 3c) in intercellular contacts. However, stable expression of Snail induces a dramatic conversion to a completely undifferentiated fibroblastic phenotype. MDCK cells transfected with Snail lose the ability to grow as a monolayer and to inhibit by contact. Instead, these cells form overlying networks with extremely long membranous extensions (FIG. 3d). Analysis of E-cadherin and plakoglobin expression showed the loss of both molecules in MDCK cells transfected with Snail (FIGS. 3e and f). Additionally, stable expression of Snail in MDCK cells induced a strong migratory behaviour, which was demonstrated by tests of wound-healing in cultures (FIG. 4).

Snail is Expressed in Undifferentiated Tumours and in Invasive Regions of Epidermoid Carcinomas.

Analysis of the endogenous expression of Snail by RT-PCR in a panel of cell lines with varying E-cadherin expression demonstrated an inverse correlation between the expression of both molecules and a relationship between the expression of Snail and their invasive and metastatic capacity (FIG. 5) E-cadherin was observed in the epithelial, non-tumoral MCA3D cell line and in the PCV tumoral cell line, which in spite of its tumoral origin showed no invasive or metastatic capacity. However, the presence of Snail was not found in any of the cell lines. In contrast, in the tumour cell lines with invasive and metastatic capacity, HaCa4 and CarB, the absence of E-cadherin is associated with the presence of Snail.

Expression of Snail was analysed by in situ hybridisation in epidermoid tumours induced in immunodepressed mice, either by different cell lines or by chemical treatment of the mouse's skin. In both cases, high expression of Snail was observed in undifferentiated tumours (FIGS. 6f and h) and in zones of invasion in epidermoid carcinomas (FIG. 6l) which had lost expression of E-cadherin (FIG. 6k). In contrast, no expression of Snail was detected in non-invasive, well-differentiated tumours (FIGS. 6b and 6d).

Taken together, these data demonstrate that Snail is a direct repressor of E-cadherin expression, implicated in the epithelial-mesenchymal transition which occurs during tumour invasion. The presence of Snail, therefore, is a new marker of tumour progression, specifically associated with the acquisition of the invasive and metastatic phenotype, which allows it to be used as a diagnostic marker of tumours in humans and as a guide to medical professionals in the selection and evaluation of antitumoral treatments and forms part of this invention.

Moreover, these data clearly indicate the direct inductive role of Snail in the acquisition of these characteristics of tumour invasion and metastasis, so that Snail may be considered a target protein for new antitumoral compounds. Experiments to identify new antitumoral candidates can be developed from this protein, based on cell lines transformed by the Snail protein, in which analysis of the regulation of Snail expression by an antitumoral candidate would identify new antitumoral compounds, which form part of this invention. Analysis of the regulation of Snail expression could be carried out by determining the presence or absence of Snail after contact with the antitumoral candidate, or by means of another type of signal inhibiting the Snail function in cells transformed with reporter genes, eg HIS3 and LacZ, which form part of this invention.

DESCRIPTION OF THE FIGURES

FIG. 1. Snail represses the activity of the E-cadherin promoter in epithelial cell lines. MCA3D (FIG. 1A) and PDV cells (FIG. 1B) were transfected with the native E-cadherin promoter (wt-178) or with a mutated version (mE-pal) fused to the gene marker CAT in the presence of 1 µg of control vector pcDNA3 or containing Snail. The graph shows the levels of CAT activity of the promoter. Promoter activity is expressed as a measurement relative to that of the native promoter in the presence of the control vector.

EXAMPLES

Example 1

Figure 2:
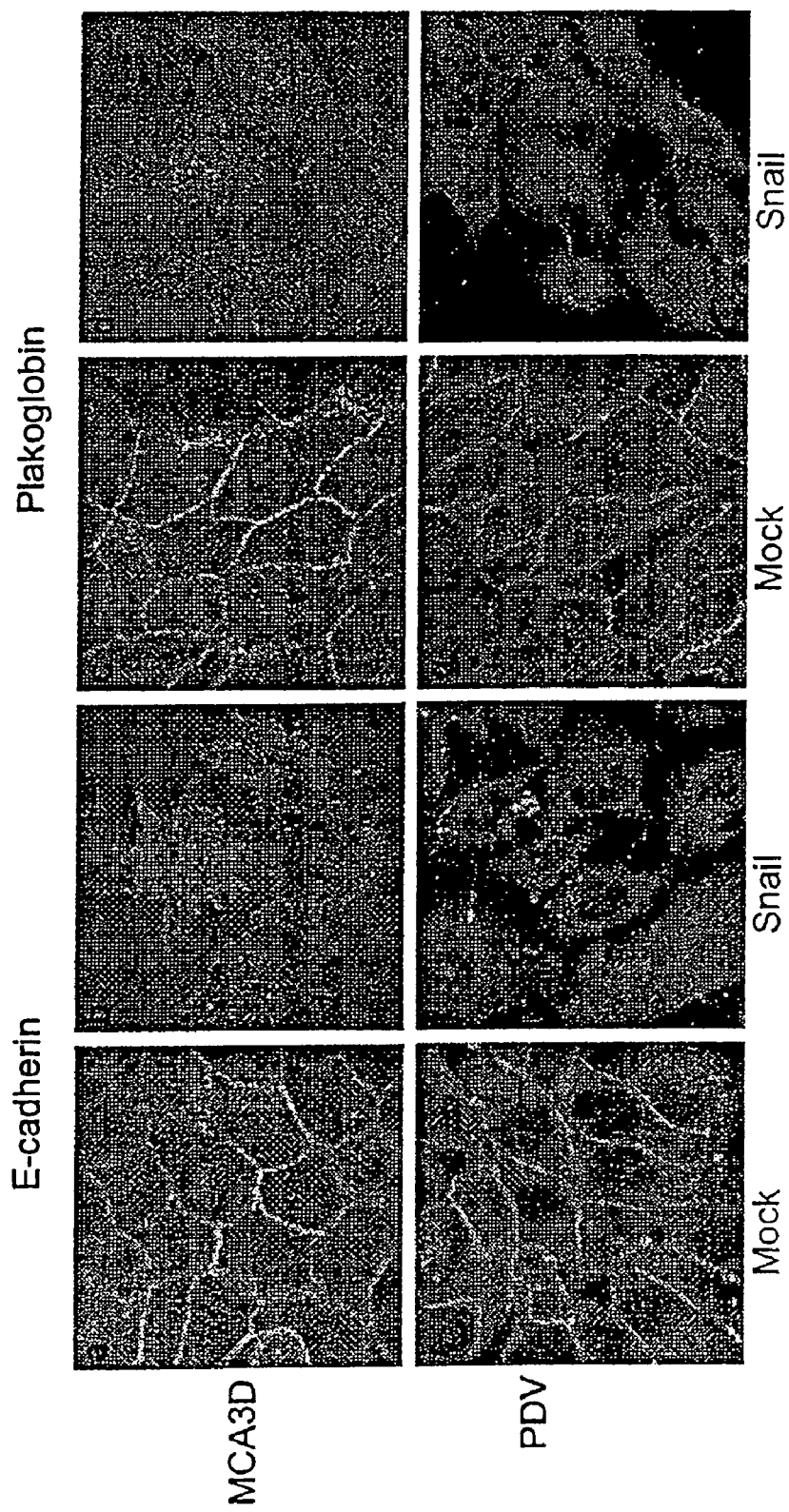
FIG. 2. Transient expression of Snail in epidermal keratinocytes induces loss of E-cadherin and plakoglobin and loss of cell-cell adhesion. MCA3D (a-d) and PDV (e-h) cells were transfected with control vector (mock, a,c,e,g) or that containing Snail cDNA (b,d,g,h) and the presence of E-cadherin and plakoglobin was analysed by immunocytochemistry visualised by confocal microscopy after 48 hours.
Figure 3:
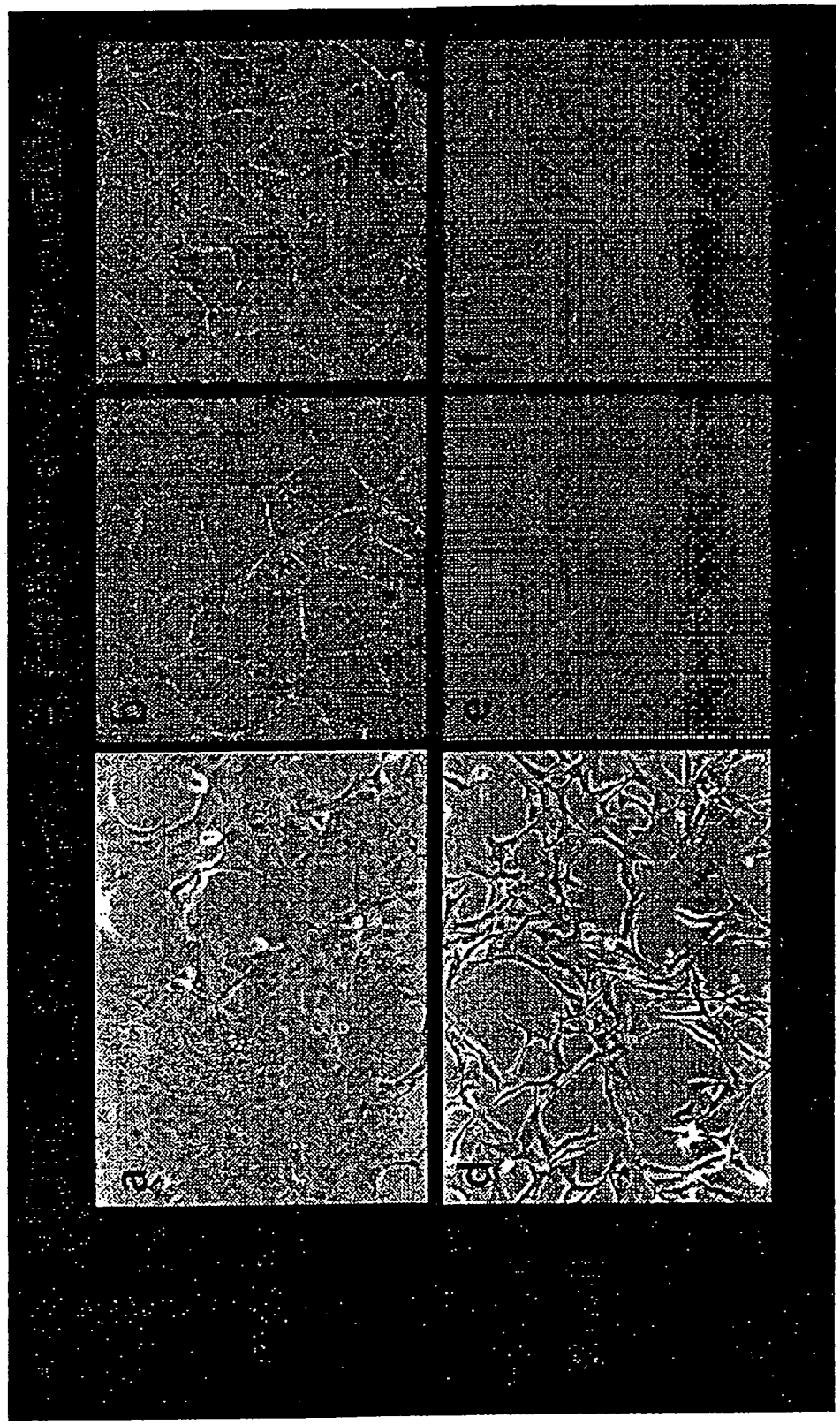
FIG. 3. Stable transfection of Snail in MDCK epithelial cells induces epithelial-mesenchymal conversion concomitant with the loss of E-cadherin and plakoglobin. Phase contrast images of cells transfected with the control vector (a) and with the vector containing Snail (d). Confocal microscopy images which show expression of E-cadherin (b,e) and plakoglobin (c,f) in control and transfected Snail cells, respectively.
Figure 4:
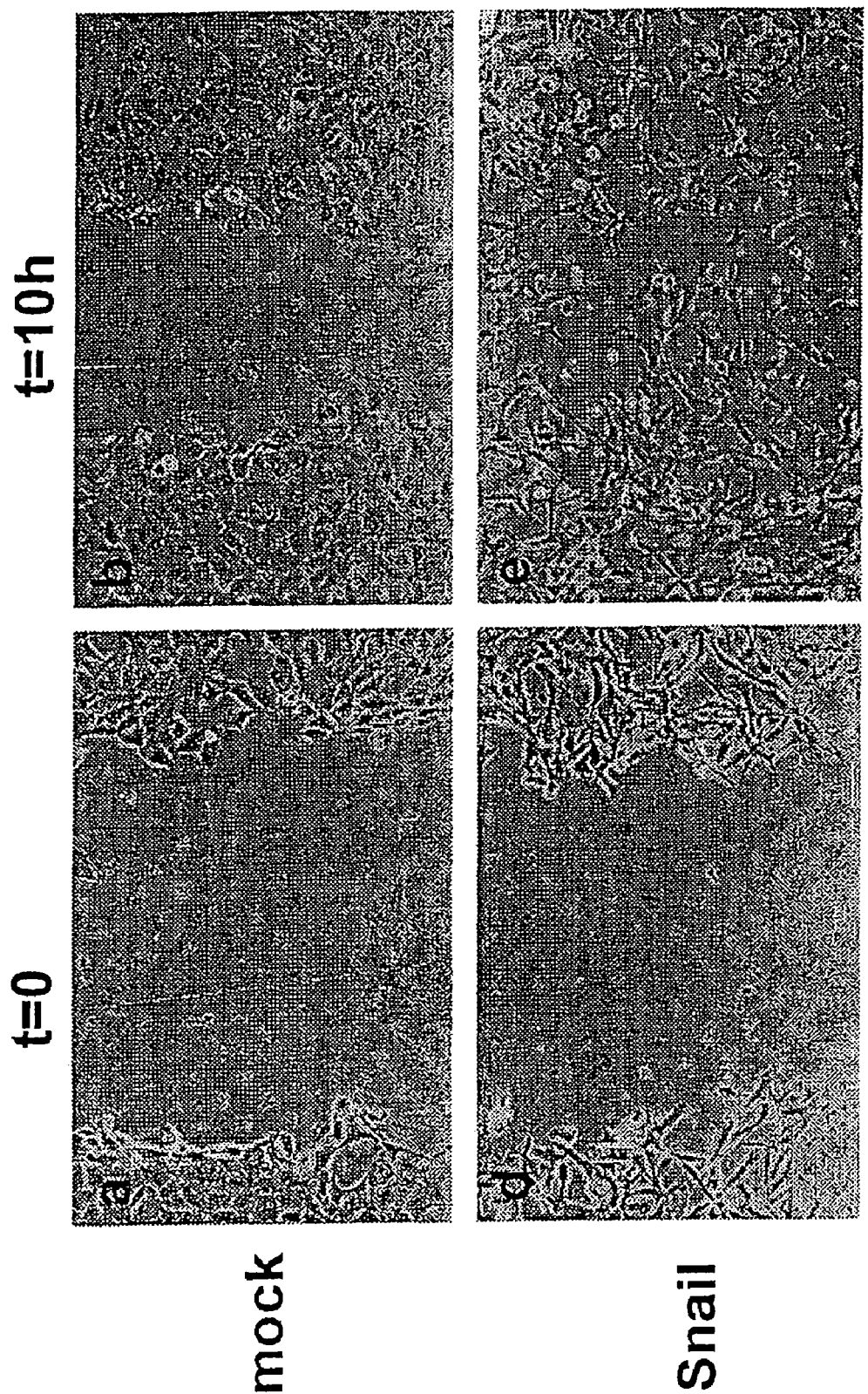
FIG. 4. Snail induces a migratory phenotype in epithelial cells. The migratory behaviour was analysed in an in vitro wound model. MDCK control cultures (mock) or cultures transfected with Snail were scratched with the tip of a pipette and photographs were taken immediately (t=0, a,d) and 10 hours later (b,e).
Figure 5:
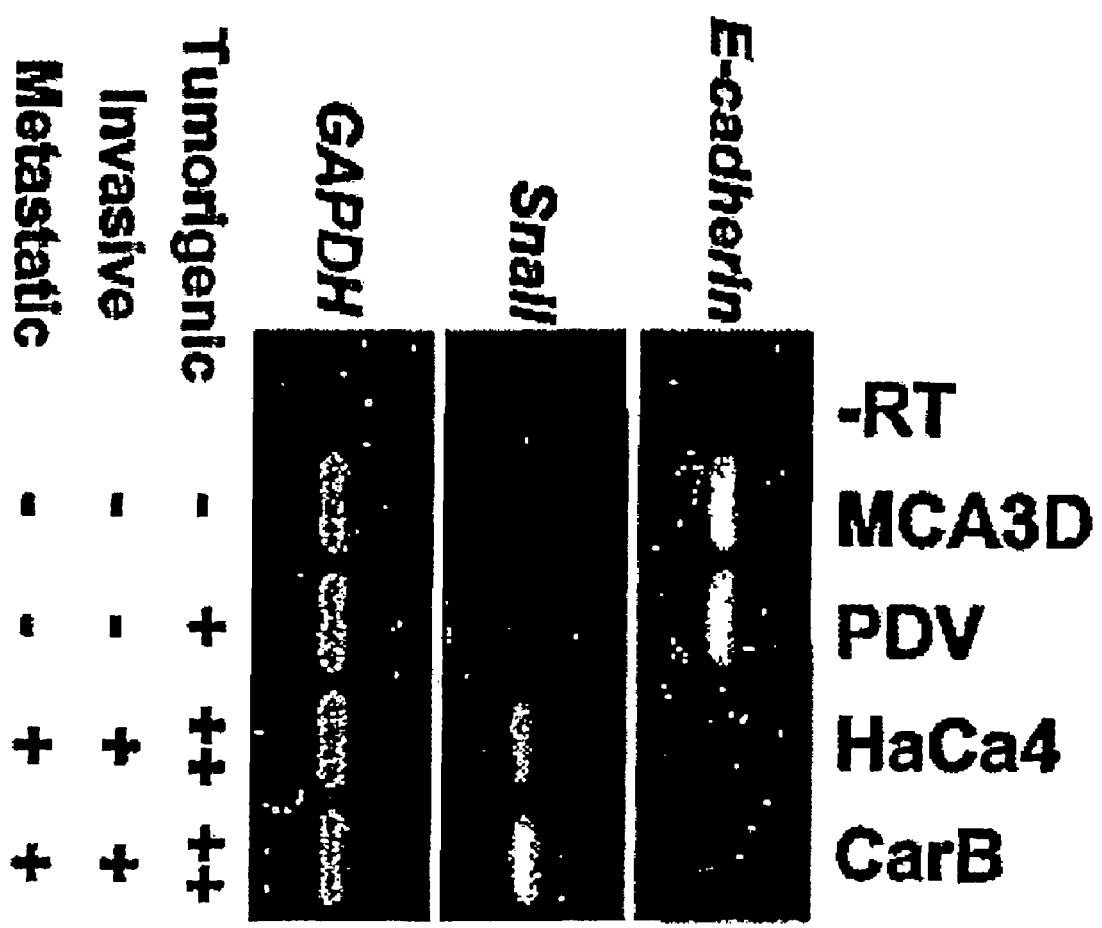
FIG. 5. Analysis of the endogenous expression of Snail by RT-PCR in a panel of cell lines. The endogenous expression of Snail is inversely correlated with that of E-cadherin in normal and transformed mouse keratinocyte cell lines.
Figure 6:
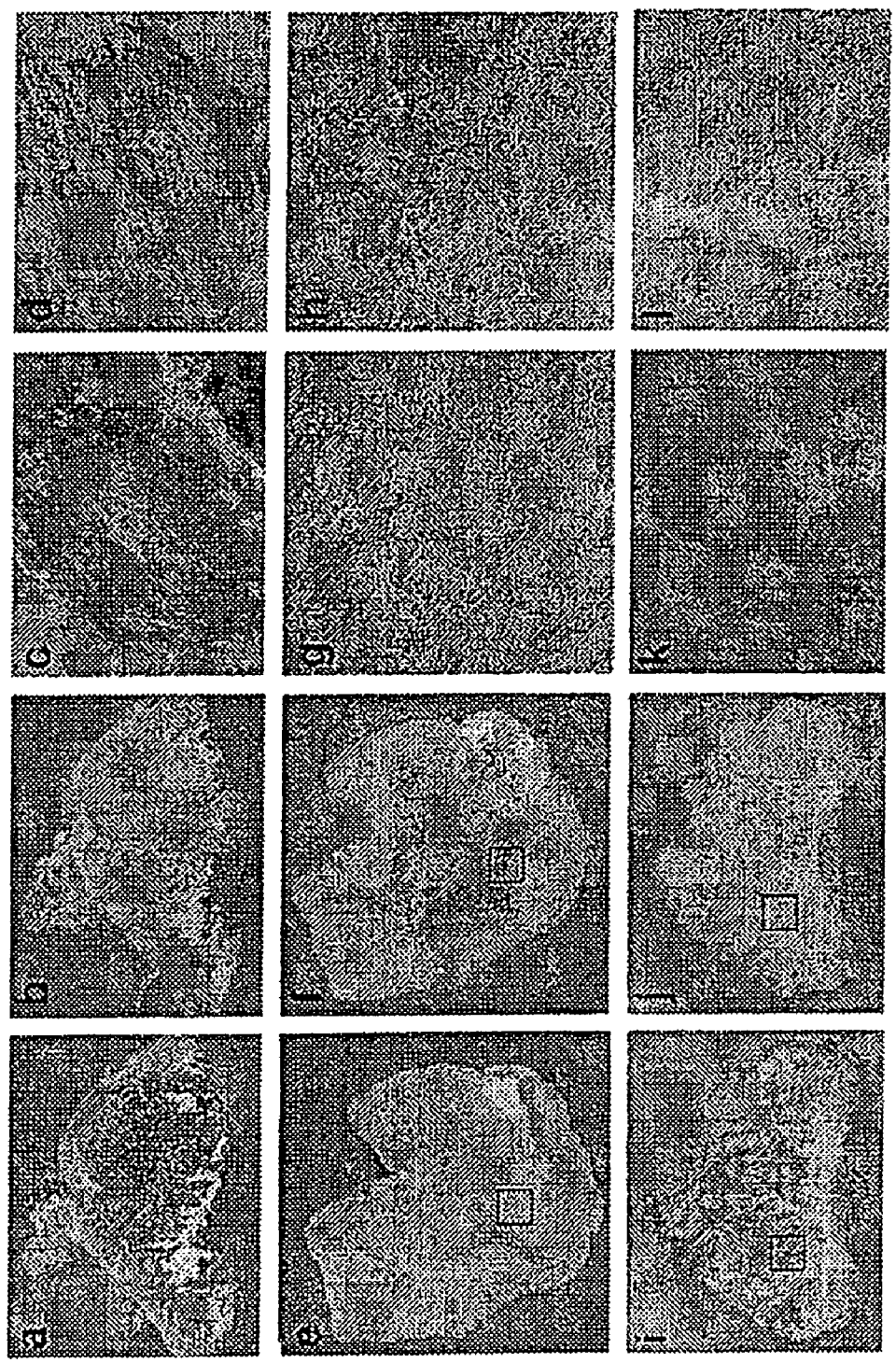
FIG. 6. Snail expression is associated with invasive carcinomas and invasive areas in epidermoid carcinomas. Tumours were induced in nude mice with PDV (a-d) or CarB (e-h) cells or by chemical treatment (i-l). They were analysed by hybridisation in situ with E-cadherin (a,c,e,g,i,k) or Snail (b,d,f,h,j,l) probes. E-cadherin is expressed in differentiated areas of epidermoid carcinomas (a,c,i,k), while there is no expression of Snail in these tumours (b,d,j). Invasive carcinomas do not express E-cadherin (e,g) but do express Snail (f,h). In chemically induced tumours, Snail expression is observed in undifferentiated invasive areas (l), which do not express E-cadherin (k).

Isolation of Snail cDNA in Mice Using the One-hybrid Technique

The oligonucleotide which contains the sequence of the E-pal element of the mouse E-cadherin promoter (CD-E) (nucleotides −90 to −70) containing targets for the restriction enzymes SalI in 5' and XhoI in 3' was ligated in direct sense for a total of 6 complete repetitions using conventional techniques, isolation in polyacrylamide gels and cloning in pHISi vector (Clontech, Palo Alto, Calif.) which contains the reporter gene HIS3 of *S. cerevisiae*, and replication elements of yeast, bacteria and appropriate selection genes. In this way, the expression of the HIS3 gene remains under the control of the multimerised E-pal element. Correct insertion of the regulatory sequences was verified by PCR, digestion with appropriate restriction enzymes and sequentiation. The bait vector thus generated was denominated pHIS-E6. The same method was used to generate vectors into which a mutant version of the E-pal element was introduced, also ligated 6 times in direct sense, in which the two central oligonucleotides, GC, were replaced by TT. The mutant bait vector generated was denominated pHIS-mE6. The bait vectors pHIS-E6 and pHIS-mE6 were independently integrated in the chromosomal locus URA3 of the yeast strain YM4271 (Clontech, Palo Alto, Calif.) by the usual techniques for transformation and selection of stable strains which maintain growth in the presence of 20 mM 3-aminotriazole (3AZT). The strains selected were denominated E-pal HIS3 (native E-pal construct) and mE-pal HIS3 (mutated E-pal construct). The yeast strain E-pal HIS3 was subjected to transformation with a commercial gene library of cDNA from NIH3T3 cells which contains different inserts of cDNA fused to the GAL4 activation domain in the pACT2 vector (Clontech, Palo Alto, Calif.), previously amplified to obtain a titre of 3×10$^6$ independent clones using conventional techniques. Transformant yeasts were selected for their ability to grow in the absence of Histidine and in the presence of 20 mM 3ATZ, and 300 independent clones were isolated. The plasmids containing the different sequences of cDNA were isolated from the transformant yeasts and were later used to transform *E. coli* (DH5α strain), recovering 221 independent *E. coli* clones, from which the corresponding plasmids were isolated. To eliminate false positives, the 221 plasmids were independently introduced in parallel into the previously generated yeast strains containing the HIS3 gene under the control of the wild E-pal element (E-pal HIS3 strain) or mutated E-pal (mE-pal HIS3 strain), selecting those plasmids which conferred growth in the absence of histidine and leucine and in the presence of 20 mM 3ATZ exclusively in the strain E-pal His3; the total number selected was 130. Inserts of these plasmids were initially analysed using digestion with various restriction enzymes and sequenced in an automatic sequencer. The sequences obtained were analysed in cDNa databanks using the BLAST/FASTA programme. 49% of the clones identified encoded the total or partial mouse Snail cDNA sequence.

Example 2

Transitory Stable Transfection of mSnail in Epithelial Cells

The complete mouse Snail cDNA sequence (mSnail) contained in one of the clones identified in the one-hybrid screening was isolated from the pACT2 vector by digestion with the restriction enzymes EcoRIy HindIII and subcloned in the EcoRI/HindIII sites of the pcDNA3 vector (Invitrogene), which contains the neo gene conferring resistance to the antibiotic G418 and was sequenced at both ends. The vector thus generated was denominated pcDNA3-mSnail.

The mouse E-cadherin promoter construct, −178, which contains the gene sequences −178 to +92 pb fusioned to the CAT reporter gene (Chloramphenicol Acetyl Transferase), and the mEpal construct (in which the two central GC nucleotides of the E-pal element were mutated by TT) have been described previously [Behrens, J., Löwrick, O., Klein, H. L. & Birchmeier, W. The E-cadherin promoter: functional analysis of a GC-rich region and an epithelial cell-specific palindromic regulatory element. Proc. Natl. Acad. Sci. USA 88, 11495-11499 (1991); Hennig, G., Löwrick, O., Birchmeier, W & Behrens, J. Mechanisms identified in the transcriptional control of epithelial gene expression. J. Biol. Chem. 271, 595-602 (1996); Faraldo, M. L., Rodrigo, I., Behrens, J., Birchmeier, W & Cano, A. Analysis of the E-cadherin and P-cadherin promoters in murine keratinocyte cell lines from different stages of mouse skin carcinogenesis. Mol. Carcinog. 20, 33-47 (1997)] and were provided by Dr J. Behrens.

a) Analysis of the Activity of the E-Cadherin Promoter.

MCA3D AND PDV cells were seeded at subconfluence ($3 \times 10^5$ cells/6 cm diameter plate, P-60) in HamFl2 growth medium containing 10% foetal bovine serum (Gibco) and incubated for 24 hours at 37° C. in an incubator containing 5% $CO_2$ with a humidity of 95%. The medium was then replaced by fresh DMEM medium with 10% foetal bovine serum and kept in the incubator for a further 6 hours. The cultures underwent transfection using Lipofectamin Plus (Life Technologies), following the supplier's instructions, using 2.5 μg of construct −178, mE-pal or the control vector pCATbasic (with no promoter sequences) (Promega) and in the presence of 1 μg of pcDNA3-mSnail or the empty pcDNA3 plasmid. As an additional control, the activity of the E-cadherin promoter constructs was compared with that of the vector pCAT-control (Promega) containing the CAT reporter gene under the control of the SV-40 promoter, and thus the cells were transfected in parallel with this vector. Efficiency of transfection was analysed by cotransfection in all the cultures with 2.5 μg of the CMV-Luc plasmid which contains the luciferase reporter gene under the control of the cytomegalovirus promoter. Twenty-four hours after transfection the medium was discarded and after washing with PBS the cells were collected by gently scraping the plates and were centrifuged (2000 rpm for 4 minutes). Extracts were obtained by resuspending the cellular pellet in 100 μl of a buffer containing 10 mM phosphate pH 8.0 and subjected to 4 cycles of freezing in liquid $N_2$-thawing at 37° C. Luciferase activity was initially determined in aliquots of 5 μl using a commercial kit and a luminometer. Aliquots of the different extracts containing equivalent luciferase activities were analysed for CAT activity, using $C^{14}$-chloramphenicol (Amersham) as substrate and Acetyl-CoA (Sigma) as cofactor, following the method described previously [Faraldo, M. L., Rodrigo, I., Behrens, J., Birchmeier, W & Cano, A. Analysis of the E-cadherin and P-cadherin promoters in murine keratinocyte cell lines from different stages of mouse skin carcinogenesis. Mol. Carcinog. 20, 33-47 (1997); Rodrigo, I., Cato, A. C. B. & Cano, A. Regulation of E-cadherin gene expression during tumor progression: the role of a new Ets-binding site and the E-pal element. Exp. Cell Res. 248, 358-371 (1999)]. The CAT activity obtained in MCA3D and PDV cells for the −178 construct of the native E-cadherin promoter was 70% and 50%, respectively, of that of the pCAT-SV40 vector. The CAT activities obtained were normalised to that obtained with the −178 construct in the presence of the empty pcDNA3 vector in each cell line. Transfection assays were performed in equivalent duplicate cultures of each of the cell lines for all the experimental conditions analysed.

b) The Effect of the Expression of mSnail in the Cell Phenotype and the Expression of Epithelial Markers.

Transient transfections were performed with 2 μg of mSnail (pcDNA3-mSnail vector) and "mock" controls (empty pcDNA3 vector) in mouse keratinocyte lines MCA3D and PDV, following the procedure described previously, except that the cells were seeded on circular coverslips (1.2 cm in diameter) placed on top of the P-60 plates. At 24 and 48 hours after transfection, the glass plates corresponding to the two experimental conditions of each cell line were fixed with methanol (−20° C.) for 30 s, and were analysed for E-cadherin and plakoglobin expression by immunofluorescence [Navarro, P. et al. A role for the E-cadherin cell-cell adhesion molecule in tumor progression of mouse epidermal carcinogenesis. J. Cell Biol. 115, 517-533 (1991)]. The images were analysed using a confocal microscope (Leica).

Stable transfections of mSnail and "mock" control were carried out on the MDCK epithelial line, grown in DMEM medium, 10% foetal bovine serum, in parallel cultures and following the protocol described previously. Between 48 and 72 hours after transfection, when the cultures reached confluence, the medium was changed for fresh medium and 400 μg/ml of G418 were added, selecting the cells resistant to G418 after 2-3 weeks of growth in the presence of the antibiotic. The total population generated (the "pool") in both types of culture (mSnail and mock) was collected, and independent clones were obtained by dilution. To do this, 100 cells of each type of population were seeded on P-100 plates (10 cm diameter) and grown in DMEM medium, 10% foetal bovine serum and 400 μg/ml of G418. Independent colonies resistant to G418 were obtained after a further 2-3 weeks, and these were isolated by trypsinisation using cloning cylinders (internal diameter 5 mm) and amplified by successive passages on culture plates of increasing size (T6->F12.5->F25->F75), maintaining antibiotic pressure in all phases of the culture. A total of 10 independent clones were isolated from the mSnail transfection and 6 independent clones from the mock transfection. The different clones were analysed for E-cadherin and plakoglobin expression by immunofluorescence (confocal microscope analysis) and immunotransference, and for mSnail expression by RT-PCR after extraction of the RNA-polyA+ of the different clones and the use of appropriate amplimers to amplify a fragment of 388 base pairs, in accordance with the mSnail cDNA sequence.

Example 3

Obtaining Tumours a) Tumours Induced in Immunodepressed Mice by Cell Lines.

Tumours were induced in 8-week-old athymic male nu/nu mice of the BalC strain by subcutaneous injection of PDV, HaCa4 or CarB cells, as described previously [Navarro, P. et al. A role for the E-cadherin cell-cell adhesion molecule in tumor progression of mouse epidermal carcinogenesis. J. Cell Biol. 115, 517-533 (1991)]. The different cell lines grew to confluence in F75 bottles, and were trypsinised and resuspended in phosphate buffered saline (PBS) at a density of $1\times10^7$ cells/ml in PBS. The cells were subcutaneously injected into both flanks of each mouse ($1\times10^6$ cells/injection site) using insulin syringes and 25 gauge hypodermic needles. Usually 3 animals were inoculated for each cell line (6 injection sites/line). The animals were obtained from the IFA-CREDO production unit (France) and were kept in sterile conditions in the installation specifically intended for such animals in the animal house of the Instituto de Investigaciones Biomédicas (IIB) in accordance with the centre's regulations for animal handling. The injected animals were observed 3 times a week; the appearance of tumours was determined by visual inspection and measurement of their size was done by caliper. The animals were sacrificed by asphyxia in ether when the external diameter of the tumours reached 1.5-2.0 cm. The tumours were removed, a fraction was fixed in formaldehyde for subsequent histological analysis, and the remainder was immediately frozen in isopentane directly cooled in a bath of liquid nitrogen or embedded in OCT (Tissue Tek). The samples were stored at −70° C. for later use.

b) Induction of Tumours in Mouse Skin by Chemical Carcinogenesis.

Tumours were induced in the dorsal skin of 8-10-week-old BalC mice obtained from the production unit of the IIB animal house, using the two-stage DMBA/TPA protocol as described [Cano, A. et al. Expression pattern of the cell adhesion molecules E-cadherin, P-cadherin and integrin is altered in pre-malignant skin tumors of p53-deficient mice. Int. J. Cancer 65, 254-262 (1996)]. One week before the start of the experiment, the backs of the animals (20 in total) were shaved, after which a single dose of the carcinogen dimethylben(z)anthracene (DMBA) at a concentration of 50 μg/ml dissolved in acetone was applied. A week later, the promotion was begun by topical application of phorbol tetradecanoylphorbolacetate at a concentration of 50 μg/ml dissolved in ethanol. The TPA was applied every 3 days for a total of 30 weeks. The animals were kept under weekly observation for a total of 50 weeks. At the end of 10 weeks of treatment with TPA the appearance of the first papilloma-type tumours was detected, and these continued to appear throughout the treatment and subsequently, at an average rate of 5-6 tumours per mouse. A small proportion of the papillomas (5%) progressed to carcinomas after the end of the TPA treatment. The animals were sacrificed at different intervals and the tumours were extracted and frozen as previously described.

The invention claimed is:

1. A method of altering the invasive and metastatic capacity of isolated epithelial cells said method comprising transfecting said cells with an expression vector comprising a polynucleotide encoding a full-length Snail, protein or a partial sequence thereof binding to E-cadherin promoter, thereby up-regulating expression of Snail in the cells, and up-regulation of said expression of Snail, by said polynucleotide causing an alteration of the invasive and metastatic capacity of said cells.

2. A method according to claim 1, wherein the cells are of an MCA3D, PDV or MDCK cell line.

3. A method according to claim 1, wherein the cells display a change in morphology as a result of said up-regulating of Snail expression in the cells.

4. A method according to claim 3, wherein the cells acquire membranous extensions.

\* \* \* \* \*